US010519204B2

(12) United States Patent
Patinier

(10) Patent No.: US 10,519,204 B2
(45) Date of Patent: Dec. 31, 2019

(54) METHOD FOR EXTRACTING SOLUBLE PROTEINS FROM MICROALGAL BIOMASS

(71) Applicant: Corbion Biotech, Inc., South San Francisco, CA (US)

(72) Inventor: Samuel Patinier, Quesnoy sur Deule (FR)

(73) Assignee: CORBION BIOTECH, INC., South San Francisco, CA (US)

( * ) Notice: Subject to any disclaimer, the term of this patent is extended or adjusted under 35 U.S.C. 154(b) by 82 days.

(21) Appl. No.: 15/322,189

(22) PCT Filed: Jul. 16, 2015

(86) PCT No.: PCT/FR2015/051941
§ 371 (c)(1),
(2) Date: Dec. 27, 2016

(87) PCT Pub. No.: WO2016/009146
PCT Pub. Date: Jan. 21, 2016

(65) Prior Publication Data
US 2017/0137477 A1  May 18, 2017

(30) Foreign Application Priority Data
Jul. 18, 2014 (FR) ..................... 14 56946

(51) Int. Cl.
C07K 14/405 (2006.01)
A61K 36/02 (2006.01)
A01N 65/00 (2009.01)
C07K 1/14 (2006.01)
C07K 1/34 (2006.01)
C07K 1/36 (2006.01)
C12N 1/12 (2006.01)
A23J 1/00 (2006.01)

(52) U.S. Cl.
CPC ............ *C07K 14/405* (2013.01); *A23J 1/009* (2013.01); *C07K 1/14* (2013.01); *C07K 1/145* (2013.01); *C07K 1/34* (2013.01); *C07K 1/36* (2013.01); *C12N 1/12* (2013.01)

(58) Field of Classification Search
CPC ................................... C12N 1/00; C12N 1/12
USPC .................. 435/41, 257.1, 257.3; 424/184.1
See application file for complete search history.

(56) References Cited

U.S. PATENT DOCUMENTS

| 4,564,526 A | 1/1986 | Takashima |
| 5,330,913 A | 7/1994 | Nakayama |
| 5,547,699 A | 8/1996 | Iizuka et al. |
| 5,792,631 A | 8/1998 | Running |
| 2007/0099280 A1 | 5/2007 | Barclay |
| 2010/0233761 A1 | 9/2010 | Czartoski et al. |
| 2010/0297292 A1 | 11/2010 | Brooks et al. |
| 2010/0297295 A1 | 11/2010 | Brooks et al. |
| 2010/0297296 A1 | 11/2010 | Brooks et al. |
| 2010/0297323 A1 | 11/2010 | Brooks et al. |
| 2010/0297325 A1 | 11/2010 | Brooks et al. |
| 2010/0297331 A1 | 11/2010 | Brooks et al. |
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2012/0128851 A1 | 5/2012 | Brooks et al. |
| 2013/0122180 A1 | 5/2013 | Brooks et al. |
| 2014/0212570 A1 | 7/2014 | Norris et al. |
| 2016/0046900 A1 | 2/2016 | MacQuart et al. |
| 2016/0177257 A1 | 6/2016 | Patinier |
| 2016/0324167 A1 | 11/2016 | Brooks et al. |
| 2017/0081630 A1 | 3/2017 | Passe et al. |
| 2017/0152294 A1 | 6/2017 | Patinier |
| 2018/0000116 A1 | 1/2018 | Guillemant et al. |
| 2018/0007932 A1 | 1/2018 | Patinier |
| 2018/0139993 A1 | 5/2018 | Le Ruyet et al. |
| 2018/0139994 A1 | 5/2018 | Brooks et al. |
| 2018/0223245 A1 | 8/2018 | Passé |

FOREIGN PATENT DOCUMENTS

| CN | 101352249 | | 1/2009 |
| CN | 2 924 126 | A1 | 5/2009 |
| FR | 3 008 873 | A1 | 10/2014 |
| FR | 3 008 712 | A1 | 1/2015 |

(Continued)

OTHER PUBLICATIONS

Non-Final Rejection, dated Oct. 3, 2017, in U.S. Appl. No. 15/126,370.
Non-Final Rejection, dated Mar. 26, 2018, in U.S. Appl. No. 15/546,206.
Non-Final Rejection, dated Jun. 1, 2018, in U.S. Appl. No. 15/546,236.
Non-Final Rejection, dated Jun. 18, 2018, in U.S. Appl. No. 15/322,199.
International Search Report, dated Jun. 19, 2015, from International Patent Application No. PCT/FR15/50658, including English Translation.

(Continued)

*Primary Examiner* — Rodney P Swartz
(74) *Attorney, Agent, or Firm* — Leydig, Voit & Mayer, Ltd

(57) ABSTRACT

A method for preparing a protein isolate of the biomass of microalgae of the genus *Chlorella*, includes the following steps: supplying a microalgal biomass produced by fermentation, washing the biomass so as to eliminate the soluble interstitial compounds and concentrating the biomass, mechanically grinding the washed and concentrated biomass in a horizontal ball grinder-type system in order to produce an emulsion, destructuring the emulsion thus produced, triple-phase separation so as to separate the soluble fraction from the fractions containing the lipids and the cell debris, recovery of the soluble fraction thus produced in order to produce the soluble protein isolate, then evaporation, pasteurization and atomization of the protein isolate.

10 Claims, No Drawings

(56) References Cited

FOREIGN PATENT DOCUMENTS

| | | | | |
|---|---|---|---|---|
| JP | 360075244 | | 10/1983 | |
| JP | H 0975094 | | 3/1997 | |
| JP | 409252707 | A | 9/1997 | |
| SU | 731 935 | A1 | 5/1980 | |
| WO | WO 98/015581 | A1 | 4/1998 | |
| WO | WO 2006/095964 | | 9/2006 | |
| WO | WO 2010/104922 | | 9/2010 | |
| WO | WO 2010/120923 | A1 | 10/2010 | |
| WO | 2011/057406 | A1 | 5/2011 | |
| WO | WO 2011/057406 | A1 | 5/2011 | |
| WO | WO-2011057406 | A1 * | 5/2011 | ............ A23J 1/006 |
| WO | WO 2011/130578 | A2 | 10/2011 | |
| WO | WO 2014/117163 | A1 | 7/2014 | |
| WO | WO 2014/154787 | | 10/2014 | |
| WO | WO 2015/001261 | | 1/2015 | |
| WO | WO 2015/007997 | | 1/2015 | |
| WO | WO 2015/079169 | | 6/2015 | |
| WO | WO 2015/140467 | | 9/2015 | |
| WO | WO 2016/009145 | | 1/2016 | |
| WO | WO 2016/009146 | | 1/2016 | |
| WO | WO 2016/120549 | | 8/2016 | |

OTHER PUBLICATIONS

Written Opinion of the Searching Authority, dated Jun. 19, 2015, from International Patent Application No. PCT/FR15/50658, including English Translation.

International Search Report, dated Oct. 6, 2015, from corresponding PCT Application, (International Patent Application No. PCT/FR2015/051940, filed Jul. 16, 2015).

Written Opinion, dated Oct. 6, 2015, from corresponding PCT Application, (Intentional Patent Application No. PCT/FR2015/051940, filed Jul. 16, 2015).

Written Opinion, dated Oct. 9, 2015, from corresponding PCT Application, (Intentional Patent Application No. PCT/FR2015/051941, filed Jul. 16, 2015).

International Search Report, dated Mar. 29, 2016, from International Patent Application No. PCT/FR16/50139, including English Translation.

Written Opinion of the Searching Authority, dated Mar. 29, 2016, from International Patent Application No. PCT/FR16/50139, including English Translation.

International Search Report, dated Mar. 23, 2016, from International Patent Application No. PCT/FR16/50138, including English Translation.

Written Opinion of the Searching Authority, dated Mar. 23, 2016, from International Patent Application No. PCT/FR16/50138, including English Translation.

Baker, J.E., et al., "Assimilation of Ammonia by Nitrogen-Starved Cells of Chlorella Vulgaris." Plant Physiology, (Mar. 1961), vol. 36(2), pp. 208-212.

Becker, E.W., "Micro-algae as a source of protein," Biotechnology Advances,vol. 25; No. 2, pp. 207-201, (Jan. 26, 2007).

Belasco, Warren, "Algae Burgers for a Hungry World? The Rise and Fall of Chlorella Cuisine," Technology and Culture, 38(3):608-634, (1997).

Brown, M.R., et al. "Biochemical composition of microalgae from the green algal classes Chlorophyceae and Prasinophyæae. 1. Amino acids, sugars and pigments" Journal of Experimental Marine Biology and Ecology, (Oct. 12, 1992), 161(1), 91-113.

Chacón-Lee, T.L. and G.E. González-Mariño, "Microalgae for "Healthy" Foods—Possibilities and Challenges", Comprehensive Reviews in Food Science and Food Safety, vol. 9; (Oct. 31, 2010), pp. 655-675.

Coustets, M. et al. "Flow Process ofr Electroextration of Total Proteins from Microalgae", Journal of Membrane Biology, Springer, XX, vol. 246, No. 10, Apr. 11, 2013 (Apr. 11, 2013), pp. 751-760, XP035326801, ISSN: 0022-2631, [retrieved on Apr. 11, 2013], DOI: 10.1007/S00232-013-9542-Y.

Doucha J et al.: "Influence of processing parameters on disintegration of Chlorella cells in various types of homogenizers", Applied Microbiology and Biotechnology, Springer, Berlin, DE, vol. 81 , No. 3, Aug. 29, 2008, (Aug. 29, 2008), pp. 431-440, XPOI9654147, ISSN: 1432-0614, DOI: 10.1007/S00253-008-1660-6.

Eny, G. D. M, Amino acids in healthy Chlorella cells, (1949), JLBacteriol.,58, 269-270.

Ganeva, V., et al., "High Yield Electroextraction of Proteins from Yeast by a Flow Process." Analytical Biochemistry, vol. 315, pp. 77-84, 2003.

Grima, E. Molina, et al., "Recovery of Microalgal Biomass and Metabolites: Process Options and Economics." Biotechnology Advances, vol. 20, pp. 491-515, 2003. XP004400158, DOI: 10.1016/S0734-9750(02)00050-2.

Haas, D.P., On certain peptides occurring in marine algae. Biochem. J., (1950), 46, 503-505.

Hattori, A., Studies on the metabolism of urea and other nitrogenous compounds in Chlorella ellipsoidea. II. Changes on levels of amino acids and amides during the assimilation of ammonia and urea by nitrogen-starved cells. J. Biochem., (1958), Tokyo, 45, 57-64.

Kanazawa, C.T., Changes of amino acid composition of Chlorella cells during their life cycle. Plant & Cell Physiol., Jun. 29, 1964), 5, 333-354.

Kanazawa, T., et al., "New Arginne-Containing Peptides Isolated from Chlorella Cells", Plant & Cell Physiol., (1965), vol. 6, pp. 631-643.

Krüger, "Kurze Charakteristik einiger niedrerer Organismen im Saftfluss der Laubbäume," Hedwigia, 33: 241-266, (1894). Machine Translation.

Mahboob, S. et a l., "High-Density Growth and Crude Protein Productivity of a Thermotolerant Chlorella Vulgaris: Production Kinetics and Thermodynamics." Aquacult. Int., vol. 20, pp. 455-466, 2012.

Mendez, Lara et al., "Effect of High Pressure Thermal Pretreatment on Chlorella Vulgaris Biomass: Organic Matter Solubilisation and Biochemical Methane Potential." Fuel, vol. 117, pp. 674-679, 2014.

Miao et al., "Biodiesel Production From Heterotrophic Microalgal Oil," Biosource Technology, 97(06):841-846, (2006).

Miao et al., "High Yield Bio-Oil Production from Fast Pyrolysis by Metabolic Controlling of Chlorella Protothecoides," J. Biotech., 110:85-93, (2004).

Reisner, B. G. S., Gering, R. K., and J. F. Thompson. The metabolism of nitrate and ammonia by Chlorella. Plant Physiol., (1960), 35, 48-52.

Richmond, "Handbook of Microalgal Mass Culture", Biotechnology and Applied Phycology, 1986, CRC Press, Inc.

Samarasinghe, Nalin, et al., "Algal Cell Rupture Using High Pressure Homogenization as a Prelude to Oil Extraction." Renewable Energy, vol. 48, (Apr. 20, 2012) pp. 300-308, 2012.

Sansawa, H. et al., "Production of Intracellular Phytochemicals in Chlorella under Heterotrophic Conditions," Journal of Bioscience and Bioengineering, 98(6):437-444, (Jan. 1, 2004).

Shi et al., "Production and rapid extraction of lutein and the other lipid-soluble pigments from Chlorella protothecoides grown under heterotrophic and mixotrophic conditions," Nahrung, 43:109-113, (1999).

Shi, et al., "Production of biomass and lutein by Chlorella protothecoides at various glucose concentrations in heterotrophic cultures", Process Biochemistry, 34:341-347, (1999).

Syrett, P.J., "The Assimilation of Ammonia by Nitrogen-Starved Cells of Chlorella Vulgaris. Part II. The Assimilation of Ammonia to Other Compounds." Annals of Botany, vol. 17, pp. 21-36, 1953.

Syrett, P.J., "The Assimilation of Ammonia by Nitrogen-Strayed Celled of Chlorella vulgaris. Part I: The Correlation of Assimilation with Respiration", Annals of Botany, Academic Press, London, GB,(Jan. 1, 1953), vol. 17, No. 1, pp. 1-19.

Ursu, Alina-Violeta et al., "Extraction, fractionation and functional properties of proteins from the microalgae Chlorella vulgaris", Bioresource technology, vol. 157, Mar. 1, 2014 (Mar. 1, 2014), pp. 134-139, XP055108068, ISSN: 0960-8524, DOI: 10.1016/j.biotech.2014.01.071.

(56) References Cited

OTHER PUBLICATIONS

Wu et al., "A Comparative Study of Gases Generated from Simulant Thermal Degradation of Autotrophic and Heterotrophic Chlorella," Progress in Natural Science, 2(4):311-318, (1992).
Wu et al., "Comparative study on Liposoluble Compounds in Autotrophic and Heterotrophic Chlorella Protothecoides," Acta Botanica Sinica, 35(11):849-858, (1992).
Wu et al., "New Discoveries in Study on Hydrocarbons From Thermal Degradation of Heterotrophically Yellowing Algae," Science in China, 37(3):326-35, (Mar. 1, 1994).
Xiong, W., et al., "13C-Tracer and Gas Chromatography-Mass Spectromet, Analyses Reveal Metabolic Flux Distribution in the Oleaginous Microalga Chlorella Protothecoides." Plant Physiology, vol. 154, pp. 1001-1011, Oct. 2010.
Xu, H., et al., "High Quality Biodiesel Production from a Microalgal Chlorella Protothecoides by Heterotrophic Growth in Fermenters." Journal of Biotechnology, vol. 126, pp. 499-507, (2006).
Memorandum Order, *Roquette Frères, S.A. v. Solazyme, Inc., C.A.* No. 14-1442-SLR, District Court for the District of Delaware, Jan. 12, 2016.
Plaintiff and Counter-Defendant Roquette Frères, S.A.'s Reply Brief in Support of Its Motion for Stay Pending Appeal, *Roquette Frères, S.A. v. Solazyme, Inc., C.A.* No. 14-1442-SLR, District Court for the District of Delaware, Jan. 8, 2016.
Defendant and Counterclaimant Solazyme, Inc.'s Brief in Opposition to Plaintiff and Counter-Defendant Roquette Freres, S.A.'s Motion to Stay Pending Appeal, *Roquette Frères, S.A. v. Solazyme, Inc., C.A.* No. 14-1442-SLR, District Court for the District of Delaware, Jan. 6, 2016.
Declaration of Jonathan Wolfson in Support of Defendant and Counterclaimant Solazyme, Inc.'s Opposition to Plaintiff and Counterclaimant Roquette Freres, S.A.'S Motion to Stay Pending Appeal, *Roquette Frères, S.A. v. Solazyme, Inc., C.A.* No. 14-1442-SLR, District Court for the District of Delaware, Jan. 6, 2016, Redacted Public Version.
Declaration of Jeffrey M. Goehring in Support of Plaintiff and Counter-Defendant Roquette Frères, S.A.'s Brief Motion for Stay Pending Appeal, *Roquette Frères, S.A. v. Solazyme, Inc., C.A.* No. 14-1442-SLR, District Court for the District of Delaware, Dec. 28, 2015, Redacted Version Exhibit 1, BASF and Solazyme Launch the First Commercial Microalgae-Derived Betaine Surfactant, Solazyme, Inc., Jul. 28, 2015 Exhibit 2, Solazyme Bunge Renewable Oils Completes Key Redundant Power and Steam Supplies, Solazyme Bunge Renewable Oils, Jun. 30, 2015 Exhibit 3, Solazyme Receives FDA GRAS No Questions Letter for High Oleic Algae Oil, Solazyme, Inc., Feb. 24, 2015 Exhibit 4, Solazyme's (SZYM) CEO Jonathan Wolfson on Q1 2015 Results—Earnings Call Transcript, Solazyme, Inc., May 6, 2015 Exhibit 5, Solazyme's (SZYM) CEO Jonathan Wolfson on Q2 2015 Results—Earnings Call Transcript, Solazyme, Inc., Jul. 30, 2015 Exhibit 6, Solazyme's (SZYM) CEO Jonathan Wolfson on Q4 2014 Results—Earnings Call Transcript, Solazyme, Feb. 26, 2015 Exhibit 7, Redacted in Its Entirety.
Motion to Stay Pending Appeal and Order Granting Motion to Stay Pending Appeal, *Roquette Frères, S.A. v. Solazyme, Inc., C.A.* No. 141442-SLR, District Court for the District of Delaware, Dec. 28, 2015.
Memorandum of Law in Support of Motion by Roquette Frères, S.A. for a Stay Pending Appeal, *Roquette Frères, S.A. v. Solazyme, Inc., C.A.* No. 14-1442-SLR, District Court for the District of Delaware, Dec. 28, 2015.
Email dated Nov. 3, 2015, from Gerald Suh of Solazyme, Inc., to Jeffrey M. Goehring of Young & Thompson International Patent & Trademark Law (counsel for Roquette Frères, S.A.).
Letter dated Oct. 6, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the following enclosures: • Exhibits 1, 9-12, and 14-15 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc., C.A.* No. 14-01442, District Court for the District of Delaware, D.I. 141, Jun. 22, 2015, Redacted Version • Exhibits 2-8 to the Declaration of Jeffrey M. Goehring in Support of Roquette Frères, S.A.'s Brief in Support of its Motion for Summary Judgment of Solazyme, Inc.'s Claim for Misappropriation of Trade Secrets, *Roquette Frères, S.A. v. Solazyme, Inc., C.A.* No. 14-01442, District Court for the District of Delaware, D.I. 112-1, Jun. 22, 2015 • Exhibit 13 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc., C.A.* No. 14-01442, District Court for the District of Delaware, D.I. 112-2, Jun. 22, 2015 • Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc., C.A.* No. 14-01442, District Court for the District of Delaware, D.I. 112, Jun. 22, 2015 • Roquette Frères, S.A.'s Opening Brief in Support of its Motion for Summary Judgment of Solazyme, Inc.'s Claim for Misappropriation of Trade Secrets, *Roquette Frères, S.A. v. Solazyme, Inc., C.A.* No. 14-01442, District Court for the District of Delaware, D.I. 140, Jun. 22, 2015, Redacted Version.
Letter dated Nov. 2, 2015, from Jeffrey M. Goehring of Young & Thompson International Patent & Trademark Law (counsel for Roquette Frères, S.A.) to Gerald Suh of Solazyme, Inc. and R. James Balls and William E. McShane of Novak Druce Connolly Bove + Quigg LLP (counsel for Solazyme Roquette Nutritionals, LLC), which included the same enclosures included with the letter dated Oct. 6, 2015 of Cite No. CB.
Email dated Nov. 4, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC).
Opinion dated Dec. 21, 2015 in *Roquette Frères, S.A., v. Solazyme, Inc.*, Case No. 1:14-cv-01442 (D. Del. 2015) granting Solazyme's motion for an order confirming the arbitration award rendered by CPR International Institute for Conflict Prevention & Resolution on Feb. 19, 2015, in favor of Solazyme, Inc.
Youzhi Jiagong, (Jun. 8, 2007), "Oil Processing Technology (2nd edition)", Chemical Industry Press, Title page, Publication Page, Table of Contents, pp. 206-213, (in Chinese).
"Linoleic acid and α-linolenic acid are real essential fatty acids", (Mar. 1998), Title page, Publication Page, Table of Contents, Chapter 2: Essential Fatty Acids (pp. 12-13) and Chapter 15: Selection of the most suitable fatty acids (pp. 89-91), with English translation.
Bowman, Barbara A. and Robert M. Russell (eds.), "Present Knowledge in Nutrition" (1st Edition), (Oct. 2004), Title page, Publication Page, Table of Contents, p. 231 (in Chinese).
"Auxenochlorella", article from Wikipedia, Retrieved from the Internet on Mar. 23, 2016, "https://en.wikipedia.org/w/index.php?title=Auxenochlorella&oldid=711518993".
Clore, G.M. and E.M. Chance, A computer analysis of cyanide stimulated oxygen uptake in *Chlorella Protothecoides*. (Jul. 1977) FEBS Lett. 79 (2):353-356.
"Algen—Nudein ais Altmark Spezialitat (Algae noodles: a speciality from Altmark region)" in German language, and other *Chlorella* Food products, (Oct. 9, 2007), 3 pages.
Imai, Ichiro, et al. "Advanced research on Shellfish poisonings: Current Status and overview", Table of Contents, Chapters 1 and Chapter 4, 11 pages.
"Aoko's toxin", Aichi Prefectural Institute of Public Health, 6 pages. [Retrieved from the Internet Oct. 13, 2016: <URL: http://www.pref.aichi.jp/eiseiken/5f/bloom_t.html].
Lee, Yuan-Kun, "Commercial Production of microalgae in the Asia-Pacific rim", Journal of Applied Phycology, 9:403-411, (Oct. 29, 1997).
Kay, Robert A., "Microalgae as Food and Supplement", Critical Reviews in Food Science and Nutrition, 30(6):555-573 (Feb. 1991).

(56) References Cited

OTHER PUBLICATIONS

Usuki, Riichiro and Luniko Kamata,"Experimental Trials on the Role of Lipids in Good Taste and Good Body of Foods", Research reports of Shokei Gakuin College 53, May 2006, p. 85-90 (in Japanese with English Abstract).
"Chlorella Photosynthesis—Dictionary", last modified Mar. 23, 2015, Retrevied from the Internet: <URL: (http://photosyn.jp/pwiki/index.php?%E3%82%AF%E3%83%AD%E3%83%AC%E3%83%A9) with English Machine Translation.
Hirashima, Ryuta, "Framework of evaluation on inventive step requirement and significance of 'technical problem'", Patent 2010, 63(5): 34-49 (in Japanese; no translation).
Ullmann, Jorg, "The Difference between *Chlorella* vulgaris and *Chlorella* pyrenoidosa", (2006) (http://www.algomed.de/index.php?op=algenfarm_geschichte).
"History of the algae farm: Chlorella Algae—Roquette Klötze GmbH", [Retrieved from the Internet Nov. 25, 2016: <URL: (http://www.algomed.de/index.php?op=algenfarm_geschichte)].
Kirk, J. et al., "Mastitis Control Program for Prototheca Mastitis in Dairy Cows", 6 pages. <<URL: milkquality.wisc.edu/wp=content/uploads/2011/09/mastitis-control-program_prototheca-mastitis.pdf>>.
Oral Summary, dated Nov. 7, 2016, for Invalidation Hearing for Japanese Patent No. 5731982 (in Japanese).
Oral Summary by the Patentee, dated Nov. 29, 2016, for Invalidation Hearing for Japanese Patent No. 5731982 (in Japanese).
USDA National Nutrient Database (https://ndb.nal.usda.gov/ndb/).
Environmental Stresses in Non Mammalian Organisms, p. 29. with English translation.
Letter from Ray Matulka to Paulette Gaynor and Sylvester Mosley, dated Apr. 18, 2013, re: Request to Cease Evaluation of GRN 000450, Letter from Ray Matulka to Paulette Gaynor, dated Apr. 18, 2013, re: High Lipid Chlorella protothecoides S106 Flour GRAS Notification and GRAS Exemption Claim (dated Apr. 18, 2013).
Solazyme Market and Products, (2005).
Letter from Susan Cho to Susan Carlson, dated Jul. 25, 2011 and "RF1's Chlorella vulgaris GRAS Self affirmation (dated Jul. 16, 2010)."
[Retrieved from the Internet Oct. 13, 2016: <URL: http://hfnet.nih.go.jp/contents/detail105.htm] (in Chinese).
"Roquette Freres, S.A. and Solazyme, Inc. Agree to Dissolve Microalgae Join Venture", (Jun. 24, 2013) Press Release, Lestrem, France.
Standard Tables of Food Composition in Japan 2015 (Seventh Revised Edition), Table of Fatty Acid Composition, Edited by the Council for Science and Technology, the Ministry of Education, Culture, Sports, Science and Technology, (available from http://www.mext.gojp/a_menu/syokuhinseibun/1365295.htm) Retrieved from the Internet Oct. 12, 2016: <URL: (http://www.algomed.de/index.php?op=algenfarmgeschichte)] http://www.geocities.jp/jr2bvb/syokuhin/sibousan/oil_s.htm].
"'Taste' of Lipids?" Retrieved from the Internet Oct. 12, 2016: <URL: (https://sites.google.com/site/coffeetambe/coffeescience/physiology/taste/fat] with English Machine Translation.
Japanese Laid-Open Publication No. 2000-175680 (translator's note: an English language member of the same patent family: EP 1142985 (A1)).
Japanese Laid-Open Publication No. 2002-223787 (translator's note: no English language counterpart could be located).
http://mcc.nies.go.jp/strainList.do?strainId=2555&condition=Auxenochlorella+protot hecoides.
http://mcc.nies.go.jp/strainList.do?strainId=2568&condition=Auxenochlorella+protot hecoides.
*Roquette Freres S.A. v. Solazyme Inc.*, Delaware District Court, Case No. 1:14-cv-01442 District Judge Sue L. Robinson, presiding, Solazyme, Inc.'s Answer to Plaintiff Roquette Freres, S.A.'s Complaint, Petition to Confirm Arbitration Award and Counterclaims, filed Feb. 26, 2015, 29 pages.
Joint Venture and Operating agreement of Solazyme Roquette Nutritionals, LLC., dated Nov. 7, 2015.
*Solazyme, Inc.* vs. *Roquette Freres, S.A.*, Arbitration Award, dated Feb. 19, 2015.
Request for Invalidation, dated Jan. 7, 2015, for Chinese Patent Application No. 200980149978.1, 21 pages (in Chinese).
Supplemental Statement for Request for Invalidation, dated Dec. 2, 2015, for Chinese Patent Application No. 200980149978.1, 35 pages (in Chinese), including the list of submitted Counter Evidences on p. 1-2.
Notification of Acceptance of Request for Invalidation, dated Jan. 28, 2016, for Chinese Patent Application No. 200980149978.1, 4 pages (in Chinese).
Documents filed by the Petitioner—Part II, dated Apr. 29, 2015, for Chinese Patent Application No. 200980149978.1, 21 pages (in Chinese), including : • Jia, Xuan, et al., "Removal of Total nitrogen form wastewater discharge from a chemical pertilizer plant by Chlorella protothecoides USTB-01", Chinese Journal of Environmental Engineering, (Apr. 2010), 4(4):737-740 (in Chinese).
Documents filed by the Petitioner—Part III, dated May 5, 2015, for Chinese Patent Application No. 200980149978.1, 21 pages (in Chinese), including : , including : • Singelton Paul and Diana Sainsbury, "Dictionary of Microbiological and Molecular Biology, (3rd Ed. 2006)", pp. 155 (and Chinese translation thereof) • Singelton Paul and Diana Sainsbury, "Dictionary of Microbiological and Molecular Biology, (2nd Ed. 1987)", pp. 178-179 (and Chinese translation thereof).
Statement of Grounds & Particulars of Opposition, Grounds for Opposition, In the matter of Australian Patent Application No. 2009303354 in the name of Solazyme, Inc. and Opposition by *Roquette Frères, S.A.* v. *Solazyme, Inc.*, Commonwealth of Australia Mar. 3, 2016, (21 pages).
Declaration of Michael Armin Borowitzka in the matter of Australian Patent Application No. 2009303354 in the name of Solazyme, Inc. and Opposition by *Roquette Frères, S.A.* v. *Solazyme, Inc.*, Commonwealth of Australia Jun. 2, 2016, (32 pages).
• Exhibit MB-1, Federal Court of Australia, Practice Note CM7, Expert Witnesses in Proceedings on the Federal Court of Australia, commenes Jun. 4, 2013 • EXHIBIT MB-2, Michael Armin Borowitzka Curriculum Vitae • EXHIBIT MB-3, J. M. Hundley, R. B. Ing and R. W. Krauss, "Algae as Sources of Lysine and Threonine in Supplementing Wheat and Bread Diets", Science, New Series, vol. 124, No. 3221 (Sep. 21, 1956), pp. 536-537. • EXHIBIT MB-4, Krauss, Robert W., "Mass Culture of Algae for Food and Other Organic Compounds," American Journal of Botany, vol. 49, No. 4 (Apr. 1962), pp. 425-435. • EXHIBIT MB-5, Lee, Yuan-Kun, "Commercial Production of microalgae in the Asia-Pacific rim", Journal of Applied Phycology, 9:403-411, (Oct. 29, 1997) • EXHIBIT MB-6, Soong, Pinnan, "Productions and Development of *Chlorella* and *Spirulina* in Taiwan", Algae Biomass: Production and Use, Gedaliah Shelef and Carl J. Soeder (eds.), North-Holland Biomedical Press, (Dec. 1980), pp. 97-113 and title and copyright page. • EXHIBIT MB-7, Kawaguchi, Kotaro, "Microalgae Production Systems in Asia", Algae Biomass: Production and Use, Gedaliah Shelef and Carl J. Soeder (eds.), North-Holland Biomedical Press, (Dec. 1980), pp. 25-33 and title and copyright page. • EXHIBIT MB-8, Kay, Robert A., "Microalgae as Food and Supplement", Critical Reviews in Food Science and Nutrition, 30(6):555-573 (Feb. 1991).
• EXHIBIT MB-9, Raymundo et al., "Fat mimetic capacity of Chlorella vulgaris biomass in oil-in-water food emulsions stabilized by pea protein," Food Research International, 38:961-965, (Feb. 25, 2005). • EXHIBIT MB-10, Samejima, H. and J Myers, "On the Heterotrophic Growth of Chlorella *pyrenoidosa*", J. Gen Microbiol, (1958), 18:107-117.
• EXHIBIT MB-11, Aoki, Shigeji and Eiji Hase, "De- and Re-Generation of Chloroplasts in the Cells of Chlorella Protothecoides", Plant & Cell Physiol, (Sep. 5, 1964), vol. 5, pp. 473-484 [Retrieved from the internet on Jun. 7, 2013 from http://pcp.oxfordjournals.org/ by Reprints Desk ]. • EXHIBIT MB-12, Becker, E.W., "Micro-algae as a source of protein," Biotechnology Advances, 25:207-201, (Mar.-Apr. 2007). • EXHIBIT MB-13, Iwamoto, Hiroaki, "Industrial Production of Microalgal Cell-mass and Secondary Products—Major Industrial Species Chlorella", Chapter 11, Handbook of Microalgal Culture: Biotechnology and Applied Phycology, Amos Richmond (eds), (Dec. 1, 2003), pp. 255-263. • EXHIBIT MB-14,

(56) References Cited

OTHER PUBLICATIONS

Petkov et al., "Which are fatty acids of the green alga Chlorella?," Biochemical Systematics and Ecology, 35:281-285, (2007). • EXHIBIT MB-15, Gladu, Patricia K., et al. "Sterol, Fatty Acid and Pigment Characteristics of UTEX 2341, a Marine Eustigmatophyte Identified Preivously as Chlorella Minutissuma (*Chlorophyceae*)" J. Phycol., (Jun. 21, 1995), 31:774-777. • EXHIBIT MB-16, Xu et al., "High Quality Biodiesel Production From a Microalga Chlorella Protothecoides by Heterotrophic Growth in Fermenters," Journal of Biotechnology, 126(4):499-507, (May 2006). • EXHIBIT MB-17, Matsuka et al., "Changes in Contents of Carbohydrate and Fatty Acid in the Cells of Chlorella Protothecoidesduring the process of De- and Re-Generation of Chloroplasts," Plant and Cell Physiol., 7:651-662 (Sep. 24, 1966). • EXHIBIT MB-18, Xuan, J. et al., "Removal of total nitrogen from wastewater discharge from a chemical fertilizer plant by Chlorela protothecoides USTB-01", Chinese Journal of Environmental Engineering, (Apr. 2010), vol. 4, No. 4, pp. 737-740. • EXHIBIT MB-19, Australian Application No. 2009303354B2 from International Patent Application No. PCT/US2009/060692, naming Solazyme, Inc., International Patent Publication No. 2010/045368, dated Apr. 22, 2010. • EXHIBIT MB-20, Pabst, W., "Nutritional evaluation of nonsewage microalgae by the rat balance method," Arch. HyrobioL Beih, (Dec. 1978), pp. 65-70 • EXHIBIT MB-21, Urano, et al., "Effect of Osmotic Stabilizers on Protoplast Generation on Chlorella ellipsoidea Yellow/White Color Mutants", Journal of Bioscience and Bioengineering, vol. 90, No. 5, 567-569, (2000). • EXHIBIT MB-22, Kamiya, "Effects of Blue Light and Ammonia on Nitrogen Metabolism in a Colorless Mutant of Chlorella", Plant Cell Phyiol., 30(4):513-521 (1989) • EXHIBIT MB-23, Biello et al., "Biofuel of the Future: Oil from Algae," Scientific American, 2 pages, (Jan. 9, 2008).
Evidence in Support, In the matter of Australian Patent Application No. 2009303354 in the name of Solazyme, Inc. and Opposition by *Roquette Frères, S.A. v. Solazyme, Inc.*, Commonwealth of Australia, Jun. 3, 2016, (1 page).
Declaration of Young J. Suh in the matter of Australian Patent Application No. 2009303354 in the name of Solazyme, Inc. and Opposition by *Roquette Frères, S.A. v. Solazyme, Inc.*, Commonwealth of Australia, Aug. 31, 2016, (94 pages) • EXHIBIT YS1, Arbitration Award, Solazyme Inc. vs. Roquette Frères, Case 1:14-cv-O1442-SLR, Document 153, Filed Dec. 21, 2015 • EXHIBIT YS2, French Patent Publication No. FR 2 924 126, filed Nov. 28, 2007. • EXHIBIT YS3, Memorandum Opinion, Document 153, *Roquette Frères, S.A. vs. Solazyme Inc.*, Case 1:14-cv-01442-SLR, filed Dec. 21,2015.
Declaration of Craig Patch in the matter of Australian Patent Application No. 2009303354 in the name of Solazyme, Inc. and Opposition by *Roquette Frères, S.A. v. Solazyme, Inc.*, Commonwealth of Australia, Sep. 5, 2016, (22 pages) • EXHIBIT CP-1, Federal Court of Australia, Practice Note CM7, Expert Witnesses in Proceedings on the Federal Court of Australia, commences Jun. 4, 2013. • EXHIBIT CP-2, Craig Patch Curriculum Vitae.
Declaration of Craig Patch In the matter of Australian Patent Application No. 2009303354 in the name of Solazyme, Inc. and Opposition by *Roquette Frères, S.A. v. Solazyme, Inc.*, Commonwealth of Australia, Sep. 28, 2016, (42 pages). • EXHIBIT CP3, Record of Views Formed in Response to Inquires, updated Mar. 2015 (20 pages) • Exhibit CP4, Huss, V.A.R., et al., "Biochemical Taxonomy and Molecular Phylogeny of the Genus Chlorella Sensu Lato (*Chlorophyta*)1", J. Phycol. 35, 587-598 (Jan. 15, 1999).
Evidence in Answer, In the matter of Australian Patent Application No. 2009303354 in the name of Solazyme, Inc. and Opposition by *Roquette Frèeres, S.A. v. Solazyme, Inc.*, Commonwealth of Australia, Sep. 29, 2016, (1 page).
Declaration of Michael Armin Borowitzka In the matter of Australian Patent Application No. 2009303354 in the name of Solazyme, Inc. and Opposition by *Roquette Frères, S.A. v. Solazyme, Inc.*, Commonwealth of Australia, Dec. 21, 2016, (14 pages).
Evidence in Reply, In the matter of Australian Patent Application No. 2009303354 in the name of Solazyme, Inc. and Opposition by *Roquette Frères, S.A. v. Solazyme, Inc.*, Commonwealth of Australia Dec. 23, 2016, (1 page).
"Roquette's Microalgae High Lipid Algal Flour Wins Most Innovative Food Ingredient at the 2013 Fi Europe Excellence Award," www.PRnewswire.com/news-release/roquettes-migroalgae-high-lipid-algal-flour-wins-most-innovative-food-ingrediant-at-the-2013-fi-europe-excellence-awards, (Nov. 25, 2013), pp. 1-5.
Freshwater Algae Culture Collection at the Institute of Hydrobiology (FACHB-collection), certification letter by the Chinse Academy of Science, "Chlorella vulgaris", (No Date).
Zhou, Lian-ning et al. "Effects of Environmental Factors on Nitrogen and Phosphorus Removal by *Chlorella vulgaris* in Wastewater", Current Biotechnology, (Jan. 25, 2015), vol. 5, No. 1, Title page, Publication Page, Table of Contents (I Chinese and English), pp. 60-65, with English abstract.
Evidence 1, Explanation paper, filed with IP High Court Case No. H29 (gyo-ke) 10149 on Oct. 6, 2017 in Invalidation Appeal No. 2016-800012 against Japanese Patent No. 5731982, with English translation.
First Statement, Substantive Brief, filed with IP High Court Case No. H29 (gyo-ke) 10149 on Nov. 17, 2017 in Invalidation Appeal No. 2016-800012 against Japanese Patent No. 5731982, with English translation.
Second Statement, Substantive Brief, filed with IP High Court Case No. H29 (gyo-ke) 10149 on Jan. 17, 2018 in Invalidation Appeal No. 2016-800012 against Japanese Patent No. 5731982. With Explanation Paper for the Evidence. Japanese Only.
Opponent's Outline of Submissions, in the Matter of Australian Patent Application No. 2009303354 in the name of Corbion Biotech, Inc., dated Jan. 24, 2018, 48 pages.
Response to REG 5.23 Request, In the Matter of Australian Patent Application No. 2009303354 in the name of Corbion Biotech, Inc., filed Feb. 5, 2018, 18 pages. • Letter from David Sieveking, dated Jan. 24, 2018 • Statutory Declaration of Dr. Daniel Peter Sieveking, dated Jan. 24, 2018. • EXHIBIT DS-1, Kyle, David, "Production and Use of Lipids from Microalgae", Microalgal Lipids, Lipid Technology, (May-Jun. 1992), pp. 59-64. • EXHIBIT DK-2, Chen et al., "High cell density culture of microalgae in heterotrophic growth," Trends in Biotechnology, 14:421-426, (1996).
Consent to Withdraw, dated Feb. 14, 2018, for IP High Court Case No. H29 (gyo-ke) 10149, Invalidation Appeal No. 2016-800012, against Japanese Patent No. 5,731,982, in the names of TerraVia Holdings, Inc. in Japanese Only, [SOLAO043JP-0807X01JP].
Request for Withdrawal of Opposition, by Roquette Freres, to Grant of Australian Patent Application No. 2009303354, in the Name of Corbion Biotech, Inc., dated Mar. 13, 2018.
Opposition Proceedings, dated Mar. 14, 2018, Acknowledgement of the the Request for Withdrawal of Opposition, by Roquette Freres, to Grant of Australian Patent Application No. 2009303354.
Third Party Observations from Roquette Freres, dated Aug. 31, 2017, for Chinese patent for invention No. 200980149978.1 (in Japanese with English Translation).
Third Party Observations from Roquette Freres, dated Aug. 31, 2017, for Chinese patent for invention No. 201080026237.7 (in Japanese with English Translation).
Carl Safi, et al: "Influence of microalgae cell wall characteristics on protein extractability and determination of nitrogen-to-protein conversion factors", Journal of Applied Phycology, vol. 25, Aug. 8, 2012 (Aug. 8, 2012), pp. 523-529, XP002745231.
Doucha J et al.: "Influence of processing parameters on disintegration of Chlorella cells in various types of homogenizers", Applied Microbiology and Biotechnology, Springer, Berlin, DE, vol. 81, No. 3, Aug. 29, 2008 (Aug. 29, 2008), pp. 431-440, XP019654147, ISSN: 1432-0614, DOI: 10.1007/S00253-008-1660-6.
Anja Schwenzfeier et al. "Isolation and characterization of soluble protein from the green microalgae *Tetraselmis* sp." Bioresource Technology 102 (2011) 9121-9127, Laboratory of Food Chemistry, Wageningen University, The letherlands.
Carl Safi et al. "Morphology, composition, production, processing and applications of Chlorella vulgaris: A review", Renewable and

(56) References Cited

OTHER PUBLICATIONS

Sustainable Energy Reviews, vol. 35, Jul. 1, 2014 (Jul. 1, 2014), pp. 265-278, XP055138938, ISSN: 1364-0321, DOI: 10.1016/j.rser.2014.04.007.
International Search Report, dated Oct. 9, 2015, from corresponding PCT application.
"Enter the World of Microalgae," Roquette (Jun. 2014).

* cited by examiner

METHOD FOR EXTRACTING SOLUBLE PROTEINS FROM MICROALGAL BIOMASS

The present invention relates to a method for extracting soluble proteins from microalgal biomass.

The present invention also relates to the microalgal protein isolates obtained in this way.

PRESENTATION OF THE PRIOR ART

It is well known to those skilled in the art that Chlorellae are a potential source of food, since they are rich in proteins and other essential nutrients.

They are described as containing 45% of proteins, 20% of fats, 20% of carbohydrates, 5% of fibers and 10% of minerals and vitamins.

Given their abundance and their amino acid profile, microalgal proteins are thus considered as an alternative source to soy or pea proteins in food.

The protein fraction may also be exploited as a functional agent in the cosmetic, or even pharmaceutical, industries.

However, developments in food applications for microalgal proteins have not been significant, since the presence in said fractions of undesirable compounds (such as chlorophyll) leads to undesired changes in color, flavor and structure of the food compositions containing them.

To increase their potential in food applications and also to increase their commercial value, these proteins must be extracted from the microalgae without affecting their molecular structure.

"Soft" extraction techniques would therefore be necessary to isolate proteins with high solubilities and good technical and functional properties, but the rigidity of microalgal cell walls, especially of green microalgae, is fundamentally in contradiction to this, since it disrupts the extraction and integrity of the intracellular proteins.

Thus, on the contrary, conventionally "hard" physical or chemical conditions are employed to break the microalgal cell wall.

Numerous studies thus propose technologies of extraction by organic solvent type or high-pressure homogenization type.

In these technological choices, the denaturing of proteins was not however considered to be bothersome, since most of these methods were developed for purposes of analyses or intended to provide a substrate for the enzymatic digestion producing protein hydrolyzates.

However, an effective disintegration method preserving the integrity of the cell components should maximize not only the yield, but also the quality of the products extracted.

In other words, a method for optimized disintegration of the wall must for example avoid:
  chemical contamination of the targeted products,
  using a breaking energy which is too high; the latter possibly causing irreversible denaturation or degradation of the intracellular molecules of interest.

Moreover, for large-scale productions, it is important for the process chosen to be transposable to this scale.

Finally, the introduction of this cell disintegration step must be easy and must not have a negative impact on the subsequent method/treatment steps.

All these limitations influence the efficiency of the disintegration method and by the same token its energy consumption.

This is why the bead mill technology is preferred, since it is considered to be efficient for releasing intracellular proteins in their native form.

In a bead mill, the cells are agitated in suspension with small spherical particles. The breaking of the cells is caused by the shear forces, the milling between the beads, and the collisions with beads.

The description of an appropriate bead mill is, for example, given in the U.S. Pat. No. 5,330,913. These beads break the cells so as to release the cell content therefrom. A suspension of particles of smaller size than the cells of origin is then obtained in the form of an "oil-in-water" emulsion.

This emulsion is generally atomized and the water is eliminated, leaving a dry powder containing, however, a heterogeneous mixture composed of cell debris, interstitial soluble compounds, and oil.

The difficulty to be solved in the use of these cell disintegration technologies is the isolation of solely the intracellular content (to the exclusion of the membrane debris, sugars, fibers and fats) and the preservation, especially, of the quality of the protein load.

In the case of the microalga of the genus *Tetraselmis* sp, Anja Schwenzfeier et al (Bioresource Technology, 2011, 102, 9121-9127) proposed a method guaranteeing the solubility and the quality of the aminogram of the proteins isolated and with contaminants (such as coloring substances) removed, comprising the following steps:
  cell disintegration by bead mill,
  centrifugation of the milled microalgal suspension,
  dialysis of the supernatant,
  passage over ion-exchange resin,
  dialysis of the eluate,
  discoloration, then,
  washing and resuspending.

However, this laboratory method (for treating 24 g of biomass) cannot be scaled up to an industrial scale, where the bead mill method is rather used to recover a complete biomass.

Moreover, this method is not suited to microalgae which contain, in their biomass, a not insignificant lipid content (for example in *Chlorella protothecoides* the lipid content is more than 15%).

Indeed, even after this "relatively soft" breaking of the cell wall, the milled cell material is in the form of a relatively stable complex "oil in water" emulsion.

Cell components are therefore rather conventionally extracted at this stage by solvent or mechanically, but to the detriment of their integrity.

A first solution proposed by the prior art, and moreover tested by the Applicant company, consists in coupling the mechanical milling with an evaporation, in order to attempt to destabilize the emulsion, then in separating the fatty fraction by centrifugation.

However, the poor quality of the separation step (basic creaming) makes this phase separation method quite inefficient.

Even though the addition of ethanol, recommended at this stage (20-30%/raw), improves the destabilization of the emulsion, it only however enables defatting of the order of 50%, even at low yield.

Moreover, the mechanical route is particularly difficult or even impossible to carry out when the lipid fraction is bound to the protein/polysaccharide matrix.

Another solution proposes using neutral solvents. However, it has heavy constraints (quality, safety, regulations, etc.).

Subject of the Invention

The result of this is that there is an unfulfilled need for a technology for extracting and stabilizing cell components of the microalgae of interest, said cell components being released by mechanical milling.

The Applicant company has found that this need could be fulfilled by proposing an alternative method to those known from the prior art, by combining a method for mechanically milling the microalgal cells with steps for destructuring the lipid fraction produced by a treatment chosen from the group of alkaline and enzymatic treatments, followed by a step of centrifugation.

The defatted soluble fraction is then clarified by microfiltration then ultrafiltered to obtain the protein isolate.

The present invention thus relates to a method for preparing a protein isolate from the biomass of microalgae of the *Chlorella* genus, comprising the following steps:
- providing a microalgal biomass produced by fermentation,
- washing the biomass so as to eliminate the interstitial soluble compounds, and concentration,
- mechanical milling of the washed and concentrated biomass, carried out in a horizontal bead mill type system, to obtain an emulsion,
- destructuring the emulsion obtained in this way,
- triphase separation so as to separate the soluble fraction from the fractions containing lipids and cell debris,
- recovery, and optional clarification, of the soluble fraction obtained in this way, especially by microfiltration so as to remove residual insoluble substances therefrom, so as to obtain the soluble protein isolate,
- optional ultrafiltration of the clarified soluble fraction on a membrane with a cut-off threshold of less than 5 kDa, preferably of between 1 and 5 kDa, so as to obtain a soluble protein isolate,
- optional neutralization at pH 7,
- evaporation, pasteurization and atomization of said protein isolate.

Choice of the Microalgal Biomass

Preferably, the microalgae of the *Chlorella* genus are chosen from the group consisting of *Chlorella vulgaris*, *Chlorella sorokiniana* and *Chlorella protothecoides*, and are more particularly *Chlorella protothecoides*.

In one particular embodiment, the strain is *Chlorella protothecoides* (strain UTEX 250—The Culture Collection of Algae at the University of Texas at Austin—USA).

In another particular embodiment, the strain is *Chlorella sorokiniana* (strain UTEX 1663—The Culture Collection of Algae at the University of Texas at Austin—USA).

The culturing under heterotrophic conditions and in the absence of light conventionally results in the production of a *Chlorella* biomass having a protein content (evaluated by measuring the nitrogen content N×6.25) of 45% to 70% by weight of dry cells.

As will be exemplified hereinafter, this culturing is carried out in two steps:
- preculturing in a medium containing glucose and yeast extract for 72 h at 28° C. with agitation, then
- culturing for production of the biomass per se in glucose and yeast extract for more than 36 h at 28° C., with agitation and at pH 6.5 adjusted with aqueous ammonia, which results in approximately 80 g/l of biomass with a protein content (evaluated by N×6.25) of the order of 52% by weight of dry cells.

The biomass is then collected by solid-liquid separation, by frontal or tangential filtration or by any means known, moreover, to those skilled in the art.

Advantageously, the Applicant company then recommends washing and concentrating the biomass so as to eliminate the interstitial soluble compounds by a succession of concentration (by centrifugation)/dilution of the biomass.

On the industrial scale, in-line dilution and separation by centrifugation in one or two stages is advantageously chosen.

For the purposes of the invention, the term "interstitial soluble compounds" is intended to mean all the soluble organic contaminants of the fermentation medium, for example the hydrosoluble compounds such as the salts, the residual glucose, the oligosaccharides with a degree of polymerization (or DP) of 2 or 3, or the peptides.

This biomass purified in this way of its interstitial soluble compounds is then preferentially adjusted to a dry matter of between 15% and 30% by weight, preferably to a dry matter of between 20% and 30%.

For the remainder of the method of the invention, the biomass obtained in this way may be used as is, or thermally permeabilized (by a high-temperature short-time or HTST method—also developed by the Applicant company and protected in one of its as yet unpublished applications) so as to release the content of soluble peptides therefrom.

The residual proteins of this biomass may be extracted by the subsequent following steps.

Biomass Milling

The Applicant company recommends using (horizontal) bead mill technology.

More particularly, the milling may advantageously be carried out according to a method which the Applicant company has developed and protected in one of its as yet unexamined applications, in which:
- the zirconium silicate beads have an apparent density of between 2 and 3.5 kg/l, and
- the filling rate of the milling chamber is greater than or equal to 80%.

The milling is carried out in continuous mode, for example by successive passes in series.

The density of the microalgae to be milled is chosen at a level of less than 250 g/l.

At the end of milling, an emulsion is obtained.

Destructuring of the Emulsion and Separation of its Components

The separation of the components of the emulsion in order to extract the peptide or polypeptide fraction of interest therefrom requires destructuring/destabilization of the emulsion resulting from the cell milling (complex mixture of lipids, proteins—peptides and polypeptides—and cell debris).

This destructuring/destabilization of the emulsion may be facilitated:
- either by enzymatic predigestion, especially by specific proteases, by treatment with polar solvent and/or by controlled alkaline treatment targeting the protein fraction of the emulsion,
- or by adjusting the pH and the temperature, by treatment with a polar solvent and/or by enzymatic digestion, especially of cellulase type, targeting the interface with the lipid fraction of the emulsion.

Thus, the milled cell material is conditioned in a stirred reactor fitted with a low shear stirring module, so as to limit emulsification while enabling homogeneous mixing promoting the specific treatment chosen (setting a pH, action of the lytic enzyme, etc.).

For example, in the case of a treatment which aims to destabilize the emulsion by treating the protein fraction in mixture via the enzymatic route, for example by a basic protease, the temperature and the pH of the emulsion are adjusted to the reaction conditions for said protease:

the temperature is adjusted to a value of greater than 30° C., preferably of the order of 60° C., and the pH is adjusted to a value of greater than 7, preferably of the order of 8 (or even optionally of the order of 10 if only the action of pH is being utilized).

The duration of the reaction is between 2 and 8 h.

At the end of the lysis, ethanol at more than 5% (v/v) may be added to the reaction mixture as destabilizing agent for the emulsion (in the case of an oil in water emulsion).

The emulsion destabilized in this way may be (partially) split up by triphase separation, for example by centrifugation.

Thus, 3 phases are obtained:

an upper lipid cream, an aqueous/intermediate (="raw" soluble substances) soluble compounds (and residual insoluble substances) phase, and a pellet concentrating the cell debris.

The soluble fraction is essentially composed of a predominant protein fraction, soluble sugars, salts and residual lipid globules.

Membrane Separation

To release peptides and polypeptides, the method of the invention next leads to the isolation of the proteins of interest, preferably by membrane fractionation.

The Applicant company thus recommends carrying out the process in three steps:

recovery and clarification of the soluble fraction obtained in this way by microfiltration so as to remove residual insoluble substances therefrom, ultrafiltration of the clarified soluble fraction on a membrane with a cut-off threshold of less than 5 kDa, preferably of between 1 and 5 kDa, and optional neutralization at a pH of between 6 and 8, preferably at a value of 7.

Utilizing these pathways makes it possible to purify the soluble peptides and polypeptides of their residual salts and sugars.

Precipitation at the pI

Alternatively, to isolate the peptides and polypeptides of interest, the choice may be made to carry out the process in three steps:

precipitating the proteins at their pI, by adjusting the pH of the medium to a value of between 4 and 5, centrifugation or microfiltration in order to recover the precipitated proteins, and dissolving in water at a pH of between 6 and 8, preferably 7.

It should be noted that although the latter two steps make it possible, according to the method of the invention, to obtain protein isolates having a protein content of more than 80%, preferably of more than 90% by weight, they lead, by their implementational methods, to compositions distinct in nature.

Obtaining the Isolate in Powder Form

The protein isolate in soluble form obtained in this way may be:

concentrated by evaporation, pasteurized, and finally atomized.

The invention will be understood more clearly from the following examples which are intended to be illustrative and nonlimiting.

EXAMPLES

Example 1: Production of *Chlorella protothecoides* by Fed-Batch Fermentation

The strain used is *Chlorella protothecoides* UTEX 250
Preculture:
500 ml of medium in a 2 l conical flask;
Composition of the medium (in g/l):

TABLE 1

| Macro-elements (g/l) | Glucose | 40 |
| --- | --- | --- |
| | $K_2HPO_4$ | 3 |
| | $Na_2HPO_4$ | 3 |
| | $MgSO_4 \cdot 7H_2O$ | 0.25 |
| | $(NH_4)_2SO_4$ | 1 |
| | Citric acid | 1 |
| | Clerol FBA 3107 (antifoam) | 0.1 |
| Micro-elements and Vitamins (mg/l) | $CaCl_2 \cdot 2H_2O$ | 30 |
| | $FeSO_4 \cdot 7H_2O$ | 1 |
| | $MnSO_4 \cdot 1H_2O$ | 8 |
| | $CoSO_4 \cdot 7H_2O$ | 0.1 |
| | $CuSO_4 \cdot 5H_2O$ | 0.2 |
| | $ZnSO_4 \cdot 7H_2O$ | 0.5 |
| | $H_3BO_3$ | 0.1 |
| | $Na_2MoO_4 \cdot 2H_2O$ | 0.4 |
| | Thiamine HCl | 1 |
| | Biotin | 0.015 |
| | B12 | 0.01 |
| | Calcium pantothenate | 0.03 |
| | p-Aminobenzoic acid | 0.06 |

Incubation is carried out under the following conditions: duration: 72 h; temperature: 28° C.; agitation: 110 rpm (Infors Multitron incubator).

The preculture is then transferred to a 30 l Sartorius type fermenter.

Culture for Biomass Production

The medium is as follows:

TABLE 2

| Macro-elements (g/l) | Glucose | 40 |
| --- | --- | --- |
| | $KH_2PO_4$ | 1.8 |
| | $NaH_2PO_4$ | 1.4 |
| | $MgSO_4 \cdot 7H_2O$ | 3.4 |
| | $(NH_4)_2SO_4$ | 0.2 |
| | Clerol FBA 3107 (antifoam) | 0.3 |
| Micro-elements and Vitamins (mg/l) | $CaCl_2 \cdot 2H_2O$ | 40 |
| | $FeSO_4 \cdot 7H_2O$ | 12 |
| | $MnSO_4 \cdot 1H_2O$ | 40 |
| | $CoSO_4 \cdot 7H_2O$ | 0.1 |
| | $CuSO_4 \cdot 5H_2O$ | 0.5 |
| | $ZnSO_4 \cdot 7H_2O$ | 50 |
| | $H_3BO_3$ | 15 |
| | $Na_2MoO_4 \cdot 2H_2O$ | 2 |
| | Thiamine HCl | 6 |
| | Biotin | 0.1 |
| | B12 | 0.06 |
| | Calcium pantothenate | 0.2 |
| | p-Aminobenzoic acid | 0.2 |

The initial volume (Vi) of the fermenter is adjusted to 17 l after inoculation. It is brought to a final volume of approximately 20-25 l.

The parameters for performing the fermentation are as follows:

TABLE 3

| Temperature | 28° C. |
| --- | --- |
| pH | 5.0-5.2 by 28% w/w $NH_3$ |
| $pO_2$ | 20% ± 5% (maintained by shaking) |

TABLE 3-continued

| | |
|---|---|
| Shaking | Minimum 300 rpm |
| Air flow rate | 15 l/min |

When the residual glucose concentration falls below 10 g/l, glucose in the form of a concentrated solution at approximately 800 g/l is introduced so as to maintain the glucose content between 0 and 20 g/l in the fermenter.

Results

In 40 h, 80 g/l of biomass containing 52% of proteins are obtained.

Example 2. Milling the *Chlorella protothecoides* Biomass and Recovery of the Soluble Fraction—Destructuring of the Emulsion by Treatment of the Peptide and Polypeptide Fraction The biomass obtained according to example 1 is washed and concentrated by centrifugation so as to be brought to a dry matter content of 220 g/l and to a purity of more than 90% (purity defined by the ratio of the dry matter of the biomass to the total dry matter).

It is then milled by bead milling (horizontal bead mill) with zirconium silicate beads (0.6 mm diameter, apparent density 2.4).

The milled biomass is then agitated in a reactor fitted with a marine impeller and baffles. The temperature is adjusted to 60° C. and the pH to 8 with potassium hydroxide. A basic protease in combination with a cellulase are added, with these reaction conditions being maintained for a duration of 6 h.

The emulsion is then centrifuged on a triphase centrifuge which makes it possible to obtain 3 phases: an upper lipid cream, an aqueous/intermediate (="raw" soluble substances) soluble compounds (and residual insoluble substances) phase, and a pellet concentrating the cell debris.

The fraction of raw soluble substances is clarified by microfiltration. The microfiltration permeate "P1" has a titer between 55% and 70% of peptides and proteins (expressed as total amino acids) and is then ultrafiltered on a membrane with a <5 kDa cut-off threshold.

The ultrafiltration retentate "R2" obtained in this way contains more than 80% of peptides having a molecular weight of greater than or equal to 5 kDa.

The permeate "P2" contains peptides having a molecular weight of less than 5 kDa and oligosaccharides and residual salts.

This permeate "P2" can then especially be filtered on a reverse osmosis membrane (having a degree of NaCl rejection of 93%), so as to obtain:

a retentate "R3", containing peptides having a molecular weight of less than 5 kDa and oligosaccharides of DP 2, such as sucrose; and a permeate "R3", containing oligosaccharides of DP 1, salts, free amino acids and organic acids.

The protein isolate "R2" is then:

neutralized to pH 7 with potassium hydroxide, concentrated by evaporation to 35% dry matter (DM), pasteurized, then atomized.

Example 3. Milling the *Chlorella protothecoides* Biomass and Recovery of the Soluble Fraction—Destructuring of the Emulsion by Treatment of the Lipid Fraction According to the same sequence as in example 2, the milled biomass is agitated in a reactor fitted with a marine impeller and baffles. The temperature is adjusted to 50° C. without adjusting the pH (naturally between 5 and 6).

A cellulase having optimum activity in this pH and temperature range is added, with these reaction conditions being maintained for a duration of 6 h.

At the end of the reaction, the pH is adjusted to 8 before the separation into 3 phases.

The remainder of the operations is described in example 2.

The invention claimed is:

1. A method for preparing a protein isolate from the biomass of microalgae of the *Chlorella* genus, comprising:
    providing a microalgal biomass produced by fermentation of microalgae of the *Chlorella* genus, wherein the fermentation is carried out for more than 36 hours at 28° C. with agitation and at a pH of 6.5,
    washing the microalgal biomass so as to eliminate interstitial soluble compounds and concentrate the microalgal biomass,
    mechanical milling of the washed and concentrated microalgal biomass, carried out in a horizontal bead mill type system, to obtain an emulsion,
    destructuring the obtained emulsion by (i) or (ii), thus resulting in a destructured emulsion:
        (i) by enzymatic predigestion, by treatment with polar solvent, and/or by controlled alkaline treatment targeting the protein fraction of the emulsion for a duration of 2-8 hours at a temperature of more than 30° C. and a pH of greater than 7; or
        (ii) by treatment with a polar solvent, and/or by enzymatic digestion targeting the interface with the lipid fraction of the emulsion for a duration of 6 hours at a temperature of 50° C. and a pH of 5-6;
    triphase separation so as to separate the soluble fraction from the fractions containing lipids and cell debris,
    recovering the soluble fraction obtained in this way in order to obtain the soluble protein isolate, then
    evaporation, pasteurization and atomization of the protein isolate.

2. The method as claimed in claim 1, wherein the microalgae of the *Chlorella* genus are selected from the group consisting of *Chlorella vulgaris, Chlorella sorokiniana*, and *Chlorella protothecoides*.

3. The method as claimed in claim 1, wherein the triphase separation of the destructured emulsion is carried out by centrifugation.

4. The method as claimed in claim 1, wherein the soluble protein isolate is obtained from the soluble fraction by:
    clarifying the soluble fraction by microfiltration so as to remove residual insoluble substances therefrom,
    ultrafiltration of the clarified soluble fraction on a membrane with a cut-off threshold of less than 5 kDa,
    optionally, neutralizing at a pH of between 6 and 8.

5. The method as claimed in claim 1, wherein the soluble protein isolate is obtained from the soluble fraction by:
    precipitating the proteins at their pI, by adjusting the pH of the medium to a value of between 4 and 5,
    centrifugation or microfiltration in order to recover the precipitated proteins, and
    dissolving in water at a pH of between 6 and 8.

6. The method as claimed in claim 2, wherein the microalgae of the *Chlorella* genus is *Chlorella protothecoides*.

7. The method as claimed in claim 2, wherein the triphase separation of the destructured emulsion is carried out by centrifugation.

8. The method as claimed in claim 2, wherein the soluble protein isolate is obtained from the soluble fraction by:

clarifying the soluble fraction by microfiltration so as to remove residual insoluble substances therefrom, ultrafiltration of the clarified soluble fraction on a membrane with a cut-off threshold of less than 5 kDa, and optionally, neutralizing at a pH of between 6 and 8.

9. The method as claimed in claim 2, wherein the soluble protein isolate is obtained from the soluble fraction by:

precipitating the proteins at their pI, by adjusting the pH of the medium to a value of between 4 and 5, centrifugation or microfiltration in order to recover the precipitated proteins, and dissolving in water at a pH of between 6 and 8.

10. The method as claimed in claim 5, wherein the dissolving in water is carried out at a pH of 7.

* * * * *